United States Patent [19]

Wright et al.

[11] 4,093,799

[45] June 6, 1978

[54] N-ARYLIDENE-4-CHROMANAMINES

[75] Inventors: George C. Wright; Marvin M. Goldenberg, both of Norwich, N.Y.

[73] Assignee: Morton-Norwich Products, Inc., Norwich, N.Y.

[21] Appl. No.: 812,104

[22] Filed: Jul. 1, 1977

[51] Int. Cl.$^2$ .......................................... C07D 311/68
[52] U.S. Cl. .................................................... 542/422
[58] Field of Search .............................. 542/422, 423; 260/345 D

[56] References Cited

U.S. PATENT DOCUMENTS

| | | | |
|---|---|---|---|
| 3,004,969 | 10/1961 | Paige | 542/422 |
| 3,272,806 | 7/1966 | Winterstein | 542/422 |

*Primary Examiner*—Arthur P. Demers
*Attorney, Agent, or Firm*—Anthony J. Franze

[57] ABSTRACT

Certain N-arylidene-4-chromanamines are useful as gastric antisecretory agents.

3 Claims, No Drawings

N-ARYLIDENE-4-CHROMANAMINES

This invention is concerned with chemical compounds and particularly compounds of the formula:

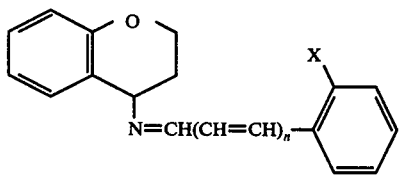

wherein $n$ is 0 or 1 and X is hydrogen or hydroxy.

The compounds of this invention possess pharmacological activity. For example, they inhibit gastric acid output in rats when administered perorally thereto at a dose of about 100 mg/kg in a suspension such as aqueous methylcellulose about one hour prior to pylorus ligation of the rat's stomach.

The compounds of this invention can be readily formulated in acceptable pharmaceutical dosage forms such as elixirs, capsules, tablets, suspensions and the like using commonly employed carriers and excipients with which there is no incompatibility.

In order that this invention may be readily available to and understood by those skilled in the art, the following examples represent the currently preferred methods of making it.

EXAMPLE I

N-Salicylidene-4-chromanamine

A 90 g (0.60 mole) portion of 4-chromanamine and 450 ml of ethanol were placed in a 2-l, 3-necked flask, equipped with a stirrer and reflux condenser fitted with a drying tube, and treated with 75 g (0.61 mole) of salicylaldehyde. The reaction mixture was refluxed for 8 hrs., stored overnight at room temperature, cooled and filtered. The yellow crystalline solid was washed with 150 ml of ethanol, ether and dried; m.p. 123°–126°. Yield: 126 g (83%).

The product was recrystallized (Darco) from 3.3 l. of methanol, washed with 300 ml of methanol, ether and dried; m.p. 124°–126°. Yield: 94 g (62%).

Anal. Calcd. for $C_{16}H_{15}NO_2$: C, 75.87; H, 5.97; N, 5.53.

Found: C, 75.71; H, 5.95; N, 5.46.

EXAMPLE II

N-Cinnamylidene-4-chromanamine

An 80 g (0.54 mole) portion of 4-chromanamine and 700 ml of ethanol were placed in a 2-l, 3-necked flask, equipped with a stirrer and reflux condenser fitted with a drying tube, and treated with 75 g (0.57 mole) of cinnamaldehyde. The reaction mixture was refluxed for 4.5 hrs., filtered hot, refrigerated overnight and filtered. A white crystalline solid was washed with 100 ml of ethanol, ether and dried; m.p. 106°–107°. Yield: 188 g (62%).

The crude product was recrystallized from 460 ml of ethanol (Darco), washed with 100 ml of ethanol, ether, and dried; m.p. 105°–106°. Yield; 71 g (50%).

Anal. Calcd. for $C_{18}H_{17}NO$: C, 82.09; H, 6.51; N, 5.32.
Found: C, 81.82; H, 6.47; N, 5.29.

What is claimed is:

1. A compound of the formula:

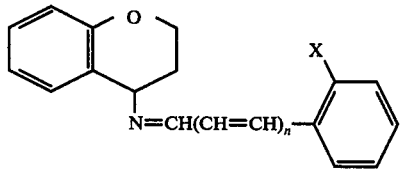

wherein $n$ is 0 or 1 and X is hydrogen or hydroxy.

2. The compound N-salicylidene-4-chromanamine.

3. The compound N-cinnamylidene-4-chromanamine.

* * * * *